US010532221B2

(12) United States Patent
Quon et al.

(10) Patent No.: US 10,532,221 B2
(45) Date of Patent: Jan. 14, 2020

(54) METHOD OF NONINVASIVE TREATMENT OF DIABETIC RETINOPATHY

(71) Applicants: Justin C. Quon, San Marino, CA (US); Matthew M. Quon-Chow, San Marino, CA (US); Joyce Y. Quon, San Marino, CA (US); Victoria A. Quon-Chow, San Marino, CA (US); Alisa S. Quon, San Marino, CA (US)

(72) Inventors: Justin C. Quon, San Marino, CA (US); Matthew M. Quon-Chow, San Marino, CA (US); Joyce Y. Quon, San Marino, CA (US); Victoria A. Quon-Chow, San Marino, CA (US); Alisa S. Quon, San Marino, CA (US)

(*) Notice: Subject to any disclaimer, the term of this patent is extended or adjusted under 35 U.S.C. 154(b) by 77 days.

(21) Appl. No.: 15/679,947

(22) Filed: Aug. 17, 2017

(65) Prior Publication Data

US 2019/0054312 A1 Feb. 21, 2019

(51) Int. Cl.
| | | |
|---|---|---|
| *A61N 5/06* | (2006.01) | |
| *A61G 10/02* | (2006.01) | |
| *A61K 31/198* | (2006.01) | |
| *A61K 45/06* | (2006.01) | |
| *A61K 33/00* | (2006.01) | |
| *A61K 31/385* | (2006.01) | |
| *A61N 5/067* | (2006.01) | |

(52) U.S. Cl.
CPC ......... *A61N 5/0622* (2013.01); *A61G 10/026* (2013.01); *A61K 31/198* (2013.01); *A61K 31/385* (2013.01); *A61K 33/00* (2013.01); *A61K 45/06* (2013.01); *A61N 2005/063* (2013.01); *A61N 2005/067* (2013.01); *A61N 2005/0635* (2013.01); *A61N 2005/0648* (2013.01); *A61N 2005/0651* (2013.01); *A61N 2005/0659* (2013.01); *A61N 2005/0662* (2013.01)

(58) Field of Classification Search
CPC ............ A61N 5/0622; A61N 2005/063; A61G 10/026; A61K 31/198; A61K 45/06
See application file for complete search history.

(56) References Cited

U.S. PATENT DOCUMENTS

| | | | | |
|---|---|---|---|---|
| 6,443,148 B1 * | 9/2002 | Rodocker | ............ | A61G 10/026 128/202.12 |
| 2007/0203173 A1 * | 8/2007 | Mudumba | ............ | A61K 31/445 514/291 |
| 2014/0336514 A1 * | 11/2014 | Peyman | ................. | A61N 5/062 600/473 |

* cited by examiner

*Primary Examiner* — Joseph M Dietrich

(57) ABSTRACT

A method for noninvasive treatment of diabetic retinopathy helps prevent and reverses diabetic retinopathy and other vascular retinopathies, such as diabetic macular edema for a patient. The method comprises administering at least 80 percent pure oxygen to a patient in an oxygen chamber or nasal cannula. The oxygen chamber includes light emitting diodes that emit a light having a wavelength between 630-700 nm wavelengths on the patient. The method also includes administering an anti-inflammatory agent; an anti-oxidant; at least one of the following: an amino acid, arginine, and citrulline; and an omega-3 fatty acids to the patient. In extreme cases of diabetic retinopathy, a cold laser therapy is also administered to the patient with a wavelength between 570 nanometers and 1000 nanometers. The combination of all the aforementioned treatment modalities and compositions that work to synergistically to achieve unexpected clinical results for prevention and reversal of diabetic retinopathy.

20 Claims, 1 Drawing Sheet

METHOD OF NONINVASIVE TREATMENT OF DIABETIC RETINOPATHY

FIELD OF THE INVENTION

The present invention relates generally to a method for noninvasive treatment of diabetic retinopathy. More so, the present invention relates to a method that prevents and reverses diabetic retinopathy and other vascular retinopathies using a series of non-invasive light and oxygen treatments and compositions to create a synergetic effect for the patient; whereby the method comprises entering, by a patient, a hyperbaric oxygen chamber defined by a minimum capability of withstanding 1.3 atmospheric absolute breathing at least 80% pure oxygen, the chamber being lined with light reflective coating and a light emitting diode having 630-700 nm wavelength; breathing, by the patient the oxygen in the chamber; directing the light from the light emitting diode towards the patient, whereby the light helps treat diabetic retinopathy and diabetic macular edema; administering an anti-inflammatory agents; administering an anti-oxidant; administering at least one of the following: an amino acid, arginine, and citrulline; administering omega-3 fatty acids; administering cold laser treatment for extreme cases of diabetic retinopathy; and whereby the combination of all the aforementioned treatment modalities works synergistically to achieve unexpected clinical results for prevention and reversal of diabetic retinopathy.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known in the art that diabetic retinopathy is a leading cause of blindness in the world. The prevalence of diabetes continues to increase throughout the world. The most recent report finds 50% of Americans have diabetes or pre-diabetes. Typically, the incidence of diabetic retinopathy is directly related to the duration of the illness. Diabetic retinopathy occurs in up to 80% of patients suffering from diabetes for over 10 years. The disease occurs even in patients with excellent control of blood sugar. Most patients can expect to suffer from the retinopathy over the course of the illness.

Currently there is no method available to prevent the onset of diabetic retinopathy. Also treatment is not available until the retinopathy becomes very severe. Then invasive treatment options will be laser photocoagulation to destroy the ischemic portion of the retina, vitrectomy, and intravitreal injections of medications such as steroids to salvage the central vision.

Generally, the protein deposits, i.e., hard exudates, are located in the foveal region. Treatment at the foveal region may be difficult with lasers without damaging the foveal region. Also laser scars may spread out over time eventually damaging the fovea causing permanent loss of central vision. Also laser photocoagulation destroys the retina and causes permanent damage to the peripheral and paracentral portion of vision. There is also a limit to the number of laser treatments that can be performed.

Generally, vitrectomy and intravitreal injections all carry severe potential complications including infection (endophthalmitis), bleeding, retinal detachment, blindness and loss of the eyeball. Even with laser photocoagulation and invasive surgical procedures, most patients can only hope for some or limited visual improvement.

Since diabetic retinopathy cannot be arrested permanently using even the most aggressive procedures, the retinopathy can continue to progress eventually causing permanent blindness. I many instances, it is much more desirable to re-perfuse the ischemic retina rather than destroying it. Therefore there is a very urgent need for a treatment method to prevent and reverse diabetic retinopathy and other vascular retinopathies using non-invasive means.

Other proposals have involved treatment of diabetic retinopathy. The problem with these treatments is that they are invasive and cause damage to the foveal region; especially with laser treatment. Even though the above cited treatments for diabetic retinopathy meet some of the needs of the market, a noninvasive method that prevents and reverses diabetic retinopathy and other vascular retinopathies using a series of non-invasive light and oxygen treatments and compositions to create a synergetic effect for the patient is still desired.

SUMMARY

Illustrative embodiments of the disclosure are generally directed to a method for noninvasive treatment of diabetic retinopathy with oxygen, lights from a light emitting diode, and compositions that help prevent and reverse diabetic retinopathy and other vascular retinopathies, such as diabetic macular edema for a patient.

In some embodiments, the method uses a series of non-invasive treatments and compositions to create a synergetic effect for the patient. Initially, the method comprises entering, by a patient, a hyperbaric oxygen chamber. The chamber is configured to enable the patient to withstand 1.3 atmospheric absolute breathing at least 80% pure oxygen. The chamber is lined with a light reflective coating and comprises a light emitting diode having 630-700 nm wavelength. The method further comprises the patient breathing the oxygen in the chamber. The method further comprises directing the light from the light emitting diode towards the patient, whereby the light helps treat diabetic retinopathy and diabetic macular edema.

In some embodiments, the method may include administering to the patient an anti-inflammatory agents to the patient. The method may also include administering to the patient an anti-oxidant to the patient. The method may also include administering, to the patient, at least one of the following: an amino acid, arginine, and citrulline. The method may also include administering to the patient omega-3 fatty acids. In extreme cases of diabetic retinopathy, a cold laser therapy is also administered to the patient with a wavelength between 570 nanometers and 1000 nanometers.

While each of the above treatment modalities and compositions helps to stabilize diabetic retinopathy, it is the combination of all the aforementioned treatment modalities and compositions that work to synergistically to achieve unexpected clinical results for prevention and reversal of diabetic retinopathy.

One objective of the present invention is to help prevent and reverses diabetic retinopathy and other vascular retinopathies, such as diabetic macular edema for a patient.

Another objective is to create a synergistic effect between various treatments and compositions to treat the diabetic retinopathy.

Yet another objective is to negate the need for laser photocoagulation to treat diabetic retinopathy.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1:
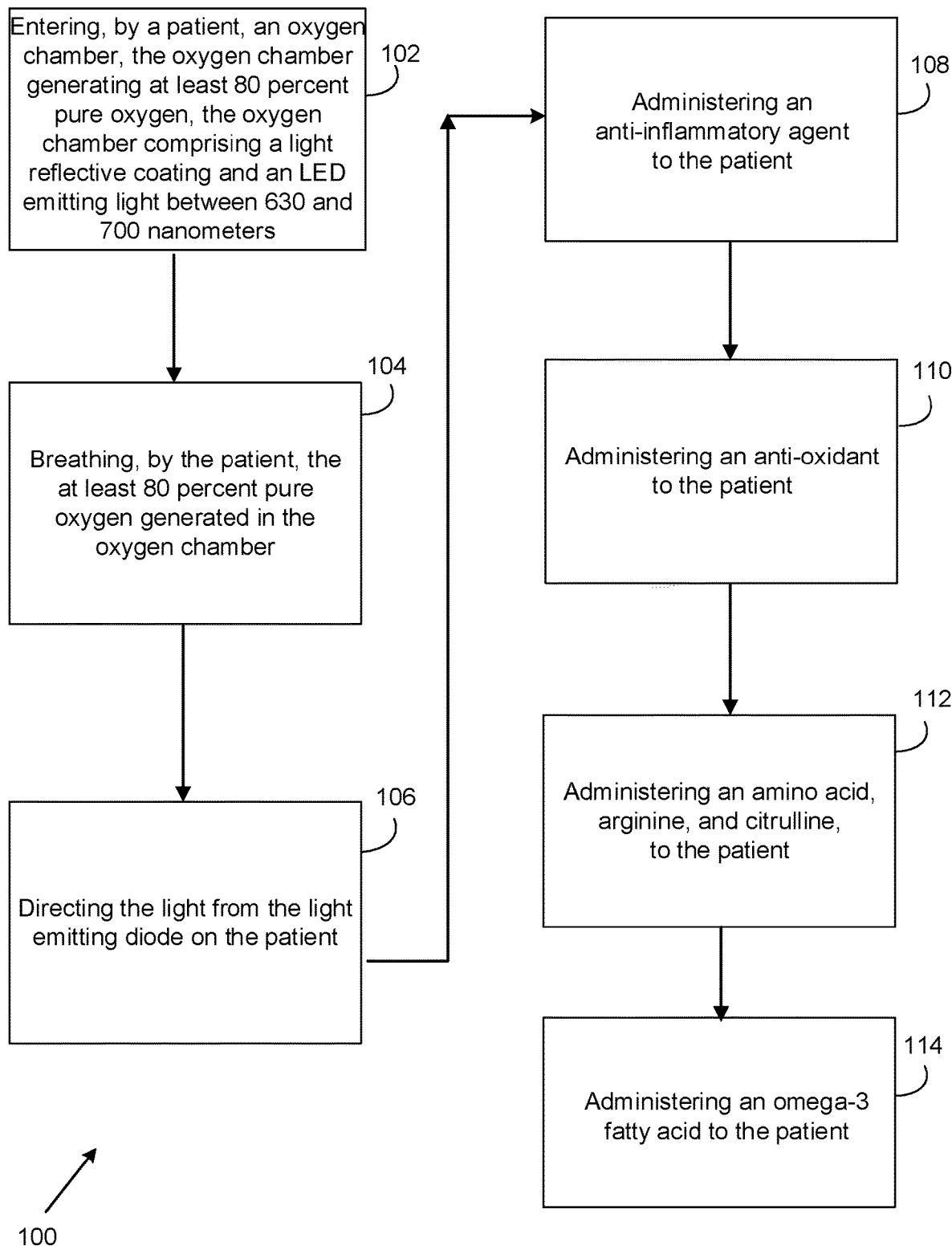
FIG. 1 illustrates a flowchart diagram of an exemplary method for noninvasive treatment of diabetic retinopathy, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A method 100 for noninvasive treatment of diabetic retinopathy is referenced in FIG. 1. The method 100 for noninvasive treatment of diabetic retinopathy, hereafter "method 100" is efficacious for preventing and reversing the effects of diabetic retinopathy and other vascular retinopathies, such as diabetic macular edema for a patient. The method 100 utilizes a combination of non-invasive treatment modalities, such as breathing 80% pure oxygen and receiving light from a light emitting diode in a hyperbaric oxygen chamber to help treat the diabetic retinopathy. Further, various compositions and agents are administered to the patient. In this manner, the central vision of the patient can be preserved.

The method utilizes an oxygen chamber to administer at least 80% pure oxygen and lights having a wavelength between 630-700 nanometers. The oxygen chamber is unique in that the walls are lined with a light reflective coating. Also, light emitting diodes are operational inside the oxygen chamber. In one embodiment, the light emitting diode emits light between 630-700 nm wavelength. The unique wavelength of the light emitting diodes is effective for treating both diabetic retinopathy and diabetic macular edema. While in the chamber, the light from the light emitting diode is focused onto the patient, or specifically to the closed eyelids of the patient.

The chamber, being a hyperbaric oxygen chamber, is also configured to emit a large quantity of oxygen for the patient to breath while inside. In one embodiment, the chamber is configured to enable the patient to withstand 1.3 atmospheric absolute breathing at least 80% pure oxygen. The amount of oxygen may be adjusted for various treatment methodologies.

While in the chamber, or after treatment in the chamber, a series of compositions are administered to the patient. Thus, in addition to the oxygen and light treatment in the chamber, a series of compositions are administered to the patient. In extreme cases of diabetic retinopathy, a cold laser therapy is also administered to the patient with a wavelength between 570 nanometers and 1000 nanometers. The combination of treatments in the chamber and administered compositions are efficacious for treating the diabetic retinopathy and other vascular retinopathies, such as diabetic macular edema.

Those skilled in the art will recognize that the underlying cause for diabetic retinopathy is ischemia in the retinal circulation. It is known that hyperglycemia triggers cellular inflammation causing obstruction in the capillaries. Further, when the red blood cells are exposed to elevated glucose levels in the blood, the red blood cell membrane becomes "stiff" making the red blood cells difficult to carry oxygen through the narrow capillary networks.

The oxygen/carbon dioxide exchange capabilities of these "sugar-coated" red blood cells are greatly reduced. The lack of oxygen supply to these ischemic areas can be seen as "capillary dropouts" on fluorescein angiography. Also, the blood-retinal barrier damage is a hallmark of diabetic retinopathy. The blood vessel endothelial cell "tight junctions" become dysfunctional with blood plasma and proteins leaking into the retinal layers. The thickened, edematous retina then causes visual impairment.

As FIG. 1 references, the method 100 uses a series of non-invasive treatments and compositions to create a synergetic effect for treating patient. Initially, the method 100 comprises a Step 102 of entering, by a patient, a hyperbaric oxygen chamber. Those skilled in the art will recognize that in a hyperbaric oxygen therapy chamber, the air pressure is increased to three times higher than normal air pressure. Under these conditions, the patient's lungs can gather more oxygen than would be possible breathing pure oxygen at normal air pressure.

In a Step 104, the method 100 comprises the patient breathing the At least 80% pure oxygen in the chamber. Such pure doses of oxygen either given via nasal cannula or hyperbaric chambers increase oxygen perfusion to the ischemic retina. In one embodiment, the hyperbaric oxygen therapy chamber is configured to enable the patient to withstand 1.3 atmospheric absolute breathing at least 80% pure oxygen. However, the oxygen chamber can be adjusted to adjust the amount of oxygen administered to the patient. In alternative embodiments, the oxygen may be administered to the patient through a nasal cannula, known in the art.

In one embodiment, the chamber is lined with a light reflective coating and comprises a light emitting diode having 630-700 nm wavelength. Thus, the method 100 further comprises a Step 106 of directing the light from the light emitting diode towards the patient. Since the method is primarily used to preserve the central vision, specific light waves are emitted towards the closed eyelids of the patient. The light helps treat diabetic retinopathy and diabetic macular edema. The light generated by the light emitting diode may be emitted either in a continuous wave, or pulsed mode to decrease retinal oxygen requirement and decrease macular edema. The patient may wear special glasses to protect the eyes while being dosed with the light from the light emitting diodes.

The elevator 100 forms different contact points with the double ladder 182, depending on the position on the double ladder 182. For example, FIG. 1A illustrates the elevator 100 in a first position 102 while engaging only with the first ladder 108. FIG. 1C illustrates the elevator 100 in the second position 106 while engaging only the second ladder 110. FIG. 1B illustrates the elevator 100 is in an overlap position 104 while engaging both ladders 108, 110 on an overlap portion 118.

Those skilled in the art will recognize that the retina is composed of rods and cones. The rods are used for black-and-white vision. Most of the oxygen needed by the retina is consumed by the rods which are located in the peripheral retina and is used for peripheral and night vision. The cones which are concentrated in the fovea/macula region are responsible for central and color vision. In treatment of diabetic retinopathy, the main goal is to preserve the central vision. Thus, when the peripheral retina is irradiated with the light from the light emitting diode, the rods are temporally disabled, thereby oxygen consumption is greatly reduced allowing the much-needed oxygen for the macula.

It is significant to note that saving the macula at the expense of damaging the peripheral retina is the reason to perform pan-retinal photocoagulation (PRP) currently. However, the main difference is that the traditional "hot" lasers used for PRP destroyed the retinal tissues permanently and the light emitting diode or "cold" lasers only do so temporally. This clinical study was performed with adult patients of different severity with Type 2 diabetes mellitus including diabetic background retinopathy without macular edema, diabetic background retinopathy with macular edema, and pre-proliferative diabetic retinopathy.

In an alternative embodiment, where the diabetic retinopathy is extreme, the method 100 further includes a step of administering a cold laser therapy to the patient with a wavelength between 570 nanometers and 1000 nanometers. Though in other embodiments, the wavelength of the laser may include between 570 nanometers and 600 nanometers and between 630 nanometers and 800 nanometers.

As discussed above, for severe cases of diabetic macular edema, the cold laser treatment, or light from the light emitting diodes may be added for treatment. The cold laser treatment, by definition, does not cause increase in tissue temperature. The cold laser treatment includes wavelengths within the range of 570-1000 nm may be used with the preferred range between 570 to 600 nm and 630 to 800 nm. The red and near-infrared wavelengths (630-800 nm) facilitate resolution of tissue edema. These wavelengths stimulate mitochondrial production of ATP for cellular repair and is best used for the peripheral retina. The yellow wavelengths (570-600 nm) are useful for nerve repair and best used for the macula.

Looking again at the flowchart of FIG. 1, the method 100 may include a Step 108 of administering to the patient an anti-inflammatory agents. The anti-inflammatory agents have the capabilities to repair the leaky endothelial cell tight-junctions and inhibit retinal neovascularization. Anti-inflammatory agents are used to remove the inflammatory oxidative reactive species to restore the vascular endothelial functions.

The method 100 may also include a Step 110 of administering to the patient an anti-oxidant to the patient. The antioxidants have the capabilities to repair the leaky endothelial cell tight-junctions and inhibit retinal neovascularization. Antioxidants are used to remove the inflammatory oxidative reactive species to restore the vascular endothelial functions.

The method 100 may also include a Step 112 of administering, to the patient, at least one of the following: an amino acid, arginine, and citrulline. The amino acids such as arginine and citrulline lead to formation of nitric oxide to provide additional oxygen to the ischemic retina. Amino acids such as arginine and citrulline both are converted by the body for nitric oxide production. These supplements provide the much-needed oxygen to the ischemic retina.

The method 100 may also include a Step 114 of administering to the patient omega-3 fatty acids. The omega-3 fatty acids have the capabilities to repair the leaky endothelial cell tight-junctions and inhibit retinal neovascularization. The omega-3 supplements carry the chemical mediators to inhibit abnormal blood vessel formation (i.e., neovascularization) in the retinal layers. In one alternative embodiment, the method 100 further includes a step of administering a turmeric and an alpha-lipoic acid to the patient. Thus, the patient can receive oral supplements of turmeric, alpha-lipoic acid, omega-3 oil, argine, and citrulline, as discussed above.

It is significant to note that, while each of the above treatment modalities and compositions helps to stabilize diabetic retinopathy, it is the combination of all the aforementioned treatment modalities and compositions that work to synergistically to achieve unexpected clinical results for prevention and reversal of diabetic retinopathy. These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A method for noninvasive treatment of diabetic retinopathy, the method comprising:
   administering, to a patient, at least 80 percent pure oxygen;
   directing a light from a light emitting diode on the patient;
   administering an anti-inflammatory agent to the patient;
   administering an anti-oxidant to the patient;
   administering at least one of the following: an amino acid, arginine, and citrulline, to the patient; and
   administering an omega-3 fatty acid to the patient,
   whereby the combination of treatment in an oxygen chamber and administered compositions and agents help to prevent and reverse the effects of diabetic retinopathy.

2. The method of claim 1, wherein the step of administering the at least 80 percent pure oxygen is delivered in a hyperbaric oxygen chamber.

3. The method of claim 1, wherein a hyperbaric oxygen chamber is defined at 1.3 atmospheric absolute.

4. The method of claim 1, further comprising a step of administering the at least 80 percent pure oxygen through a nasal cannula to the patient.

5. The method of claim 1, wherein a hyperbaric oxygen chamber is lined with a light reflective coating.

6. The method of claim 1, wherein a hyperbaric oxygen chamber comprises a light emitting diode.

7. The method of claim 1, wherein a light emitting diode emits a light having a wavelength between 630 nanometers and 700 nanometers.

8. The method of claim 1, wherein the step of directing a light from a light emitting diode on the patient, further comprises directing the light through the closed eyelids of the patient for three minutes and four times in a twenty-four hour period.

9. The method of claim 1, wherein the anti-inflammatory agents and the antioxidant help remove an inflammatory oxidative reactive species, so as to restore vascular endothelial functions.

10. The method of claim 1, wherein the arginine and citrulline are converted by the body for nitric oxide production, such that the arginine and citrulline provide oxygen to the ischemic retina.

11. The method of claim 1, wherein the omega-3 fatty acid carry chemical mediators to inhibit abnormal blood vessel formation in the retinal layers.

12. The method of claim 1, further comprising a step of administering cold laser treatment to the patient.

13. The method of claim 12, wherein the cold laser treatment comprises wavelengths between 570 nanometers and 1000 nanometers.

14. The method of claim 13, wherein a cold laser treatment comprises wavelengths between 570 nanometers and 600 nanometers.

15. The method of claim 13, wherein the cold laser treatment comprises wavelengths between 630 nanometers and 800 nanometers.

16. The method of claim 1, further comprising a step of administering a turmeric and an alpha-lipoic acid to the patient.

17. A method for noninvasive treatment of diabetic retinopathy, the method comprising:
    entering, by a patient, an oxygen chamber, the oxygen chamber configured to generate at least 80 percent pure oxygen, the oxygen chamber comprising a light reflective coating and a light emitting diode that emits light having a wavelength between 630 nanometers and 700 nanometers;
    administering the at least 80 percent pure oxygen to the patient;
    directing the light from the light emitting diode on the patient;
    administering an anti-inflammatory agent to the patient;
    administering an anti-oxidant to the patient;
    administering at least one of the following: an amino acid, arginine, and citrulline, to the patient; and
    administering an omega-3 fatty acid to the patient,
    whereby the combination of treatment in the oxygen chamber and administered compositions and agents help to prevent and reverse the effects of diabetic retinopathy.

18. The method of claim 17, further comprising a step of administering a turmeric and an alpha-lipoic acid.

19. The method of claim 17, further comprising a step of administering the at least 80 percent pure oxygen through a nasal cannula to the patient.

20. A method for noninvasive treatment of diabetic retinopathy, the method consisting of:
    entering, by a patient, a hyperbaric oxygen chamber, the hyperbaric oxygen chamber configured to generate at least 80 percent pure oxygen, the hyperbaric oxygen chamber comprising a light reflective coating and a light emitting diode that emits light having a wavelength between 630 nanometers and 700 nanometers;
    administering the at least 80 percent pure oxygen to the patient;
    directing the light from the light emitting diode to the closed eyelids of the patient;
    administering an anti-inflammatory agent to the patient;
    administering an anti-oxidant to the patient;
    administering at least one of the following: an amino acid, arginine, and citrulline, to the patient;
    administering an omega-3 fatty acid to the patient;
    administering a turmeric and an alpha-lipoic acid to the patient; and
    administering cold laser treatment to the patient, the cold laser treatment comprising wavelengths between 570 nanometers and 1000 nanometers,
    whereby the combination of treatment in the hyperbaric oxygen chamber, the light treatment, the cold laser treatment, and the administered compositions and agents help to prevent and reverse the effects of diabetic retinopathy.

* * * * *